(12) United States Patent
Daerr et al.

(10) Patent No.: US 11,963,284 B2
(45) Date of Patent: Apr. 16, 2024

(54) MAINTAINING A GIVEN FOCAL SPOT SIZE DURING A KVP SWITCHED SPECTRAL (MULTI-ENERGY) IMAGING SCAN

(71) Applicant: KONINKLIJKE PHILIPS N.V., Eindhoven (NL)

(72) Inventors: Heiner Daerr, Hamburg (DE); Bernd Rudi David, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 17/610,831

(22) PCT Filed: May 6, 2020

(86) PCT No.: PCT/EP2020/062553
§ 371 (c)(1),
(2) Date: Nov. 12, 2021

(87) PCT Pub. No.: WO2020/229254
PCT Pub. Date: Nov. 19, 2020

(65) Prior Publication Data
US 2022/0217831 A1 Jul. 7, 2022

Related U.S. Application Data

(60) Provisional application No. 62/847,387, filed on May 14, 2019.

(51) Int. Cl.
*H05G 1/58* (2006.01)
*H01J 35/14* (2006.01)
(Continued)

(52) U.S. Cl.
CPC ............. *H05G 1/58* (2013.01); *H01J 35/147* (2019.05); *H05G 1/52* (2013.01); *A61B 6/482* (2013.01); *G01N 23/046* (2013.01)

(58) Field of Classification Search
CPC .......... H05G 1/58; H05G 1/52; H01J 35/147; A61B 6/482
See application file for complete search history.

(56) References Cited

U.S. PATENT DOCUMENTS

| | | |
|---|---|---|
| 8,351,575 B2 | 1/2013 | Vogtmeier |
| 11,123,034 B2 | 9/2021 | Schaefer |
| | (Continued) | |

FOREIGN PATENT DOCUMENTS

| | | | |
|---|---|---|---|
| JP | 2011005018 A | 1/2011 | |
| WO | WO-2017046141 A1 * | 3/2017 | ............... A61B 6/42 |

OTHER PUBLICATIONS

JP 2011-005018 A with English translation (Year: 2011).*
(Continued)

*Primary Examiner* — Chih-Cheng Kao
(74) *Attorney, Agent, or Firm* — Larry Liberchuk

(57) ABSTRACT

An imaging system (202) includes an X-ray radiation source (210) configured to emit radiation that traverses an examination region. The imaging system further includes a controller (220). The controller is configured to control an X-ray tube peak voltage of the X-ray radiation source to switch between at least two different X-ray tube peak voltages during a kVp switched spectral scan. The controller is further configured to control a grid voltage of the X-ray radiation source to follow the X-ray tube peak voltage during the spectral scan. The controller adjusts the grid voltage based on a predetermined mapping between a currently applied X-ray tube peak voltage and a corresponding grid voltage for a given focal spot size, thereby maintaining the given focal spot size throughout the spectral scan.

18 Claims, 5 Drawing Sheets

(51) Int. Cl.
*H05G 1/52* (2006.01)
*A61B 6/00* (2006.01)
*G01N 23/046* (2018.01)

(56) References Cited

U.S. PATENT DOCUMENTS

| | | | |
|---|---|---|---|
| 2011/0150187 A1 | 6/2011 | Boudry | |
| 2011/0280363 A1* | 11/2011 | Zou | H01J 35/045 |
| | | | 378/111 |
| 2012/0155613 A1* | 6/2012 | Caiafa | H05G 1/10 |
| | | | 378/111 |
| 2012/0163530 A1 | 6/2012 | Sainath | |
| 2013/0202178 A1* | 8/2013 | Shechter | A61B 6/5205 |
| | | | 382/131 |
| 2013/0294578 A1* | 11/2013 | Hanlon | H05G 1/58 |
| | | | 378/111 |
| 2018/0068823 A1 | 3/2018 | Utschig | |
| 2018/0261420 A1* | 9/2018 | Holch | H01J 35/153 |

OTHER PUBLICATIONS

PCT International Search Report, International application No. PCT/EP2020/062553, dated Oct. 6, 2020.
Grajo J.R. et al., "Dual Energy CT in Practice: Basic Principles and Application", Applied Radiology, vol. 45, No. 7, pp. 6-12, Jul. 2016.

* cited by examiner

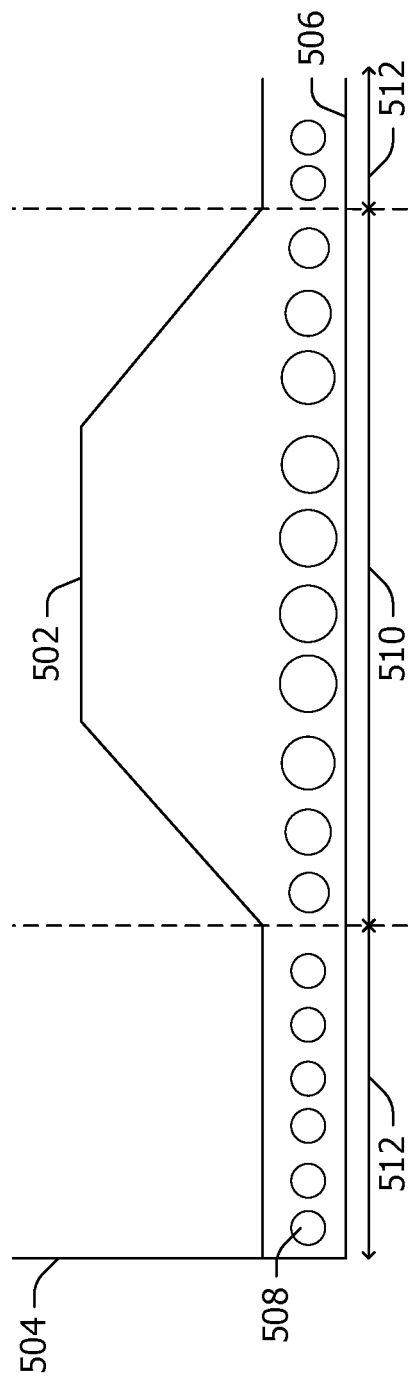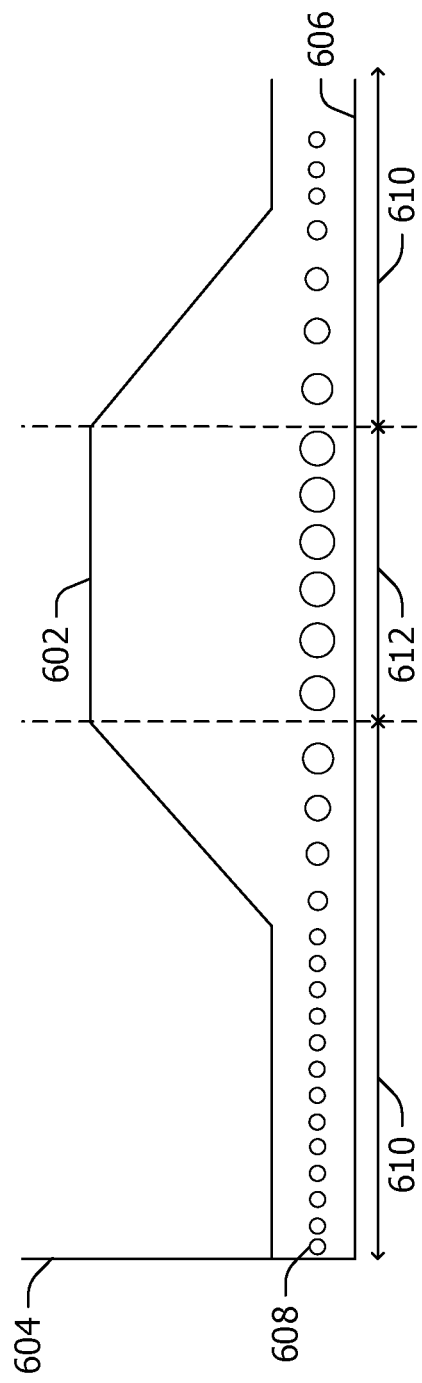

MAINTAINING A GIVEN FOCAL SPOT SIZE DURING A KVP SWITCHED SPECTRAL (MULTI-ENERGY) IMAGING SCAN

FIELD OF THE INVENTION

The following generally relates to imaging and more particularly to maintaining a given focal spot size during a kVp switched spectral (multi-energy) imaging scan and is described with particular application to computed tomography (CT).

BACKGROUND OF THE INVENTION

A computed tomography (CT) scanner generally includes an X-ray tube mounted on a rotatable gantry opposite one or more rows of detectors. The X-ray tube rotates around an examination region located between the X-ray tube and the one or more rows of detectors and emits broadband radiation that traverses the examination region. The one or more rows of detectors detect radiation that traverses the examination region and generate projection data indicative thereof. A reconstructor reconstructs the projection data to generate volumetric image data, which can be displayed, filmed, archived, conveyed to another device, etc.

FIG. 1 diagrammatically depicts certain elements of an X-ray tube 100, including a cathode 102 with a focusing cup 104 and a filament 106 and an anode 108. A tube current (mA) is applied to the filament 106, which heats the filament 106, causing the filament 106 to expel electrons (thermionic emission), creating a space charge (or cloud a negative charge) a short distance away from the filament 106. A peak tube voltage (kVp) is applied across the cathode 102 and the anode 108 and causes a beam of the electrons 110 to accelerate from the cathode 102 and impinge the anode 108. A grid voltage is applied to electrodes of the focusing cup 104 to control a size of and steer the beam of electrons 110. An interaction of the electrons 110 with the material of the anode 108 produces heat and radiation, including X-rays 112, which pass through a tube window 114, into an examination region 116, to a detector 222.

A surface area 120 of the anode 108 that receives the beam of electrons 110 is referred to as a focal spot. The size of the focal spot is one factor that affects the image quality of the volumetric image data. For example, the focal spot size affects the spatial resolution, where a smaller focal spot size results in a greater spatial resolution than a larger focal spot size, e.g., due to less focal spot blur from geometric magnification. The size of the focal spot depends on the X-ray tube voltage and the grid voltage. For a given focal spot size and a given X-ray tube voltage for a scan, the same grid voltage is applied to the focusing cup 104 the entire scan to maintain the focal spot size at a predetermined size for that X-ray tube voltage for the entire scan, e.g., to achieve a desired image quality of the volumetric image data.

The voxels of the volumetric image data are displayed using gray scale values corresponding to relative radiodensity. The gray scale values reflect the attenuation characteristics of the scanned subject and represent anatomical structures. The detected radiation also includes spectral information as the absorption of a photon by a material of a subject and/or an object is dependent on the energy of the photon traversing the material. Such spectral information provides additional information such as information indicative of the atomic, elemental or material composition of the material. However, the projection data does not reflect the spectral characteristics as the projection data are proportional to the energy fluence integrated over the energy spectrum (e.g., 40 keV to 120 keV), and the volumetric image data will not reflect the energy dependent information.

A CT scanner configured for spectral (multi-energy) imaging (a spectral CT scanner) leverages the spectral characteristics in the detected radiation to provide further information such as atomic or elemental composition information. In general, a spectral CT scanner is configured to detect different bands of X-ray radiation (instead of just the entire spectrum) and generate projection data for each of the different energy bands (instead of just the entire spectrum). In one instance, this is achieved through kVp switching. For example, with a dual-energy configuration, the X-ray tube voltage (i.e. the kVp) is switched back and forth between two kVp's, such as between a 80 kVp for odd number data acquisition periods and a second 140 kVp for even number data acquisition periods, or vice versa.

However, switching the kVp as such, for a given grid voltage, will cause the focal spot size to change, i.e. increase and/or decrease, depending on whether the kVp is switched to a higher or lower kVp, since, as described above, the focal spot size depends on both the kVp and the grid voltage. Unfortunately, this will lead to a varying spatial resolution because, as discussed above, an increased focal stop size decreases spatial resolution. Furthermore, this may introduce artifact into the reconstructed volumetric image data because the calibration table, which is created for a particular focal spot size, will not be correct for all focal spot sizes. Both of these may reduce an image (and thus diagnostic) quality of the reconstructed volumetric image data. Furthermore, a decreased focal spot may result in damage to the anode due to the concentration of electrons at small surface area on the anode.

SUMMARY OF THE INVENTION

Aspects described herein address the above-referenced problems and/or others.

For instance, the following describes an approach for controlling the X-ray tube grid voltage in coordination with the kVp during a kVp switched based spectral (multi-energy) scan to maintain a given focal spot size (within tolerance) during the spectral (multi-energy) entire scan.

In one aspect, an imaging system includes an X-ray radiation source configured to emit radiation that traverses an examination region. The imaging system further includes a controller. The controller is configured to control an X-ray tube peak voltage of the X-ray radiation source to switch between at least two different X-ray tube peak voltages during a kVp switched spectral scan. The controller is further configured to control a grid voltage of the X-ray radiation source to follow the X-ray tube peak voltage during the spectral scan. The controller adjusts the grid voltage based on a predetermined mapping between a currently applied X-ray tube peak voltage and a corresponding grid voltage for a given focal spot size, thereby maintaining the given focal spot size throughout the spectral scan.

In another aspect, a method includes controlling an X-ray tube peak voltage of an X-ray radiation source to switch between at least two different X-ray tube peak voltages during a kVp switched spectral scan, and controlling a grid voltage of the X-ray radiation source to follow the X-ray tube peak voltage during the spectral scan based on a predetermined mapping between X-ray tube peak voltages and grid voltages for a given focal spot size to maintain the given focal spot size throughout the spectral scan.

In another aspect, a computer-readable storage medium stores instructions that when executed by a processor of a computer cause the processor to: control an X-ray tube peak voltage of an X-ray radiation source to switch between at least two different X-ray tube peak voltages during a kVp switched spectral scan, and control a grid voltage of the X-ray radiation source to follow the X-ray tube peak voltage during the spectral scan based on a predetermined mapping between X-ray tube peak voltages and grid voltages for a given focal spot size to maintain the given focal spot size throughout the spectral scan.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the embodiments and are not to be construed as limiting the invention.

FIG. 5 shows a simulated plot of kVp as a function of time for dual energy scans using only a single constant grid voltages (only for a lower kVp) along with a graphic representing focal spot size.

FIG. 6 shows a simulated plot of kVp as a function of time for dual energy scans using only a single constant grid voltages (only for a higher kVp) along with a graphic representing focal spot size.

DETAILED DESCRIPTION OF EMBODIMENTS

The following describes an example imaging system configured to control the X-ray tube grid voltage in coordination with the kVp during a kVp switched based spectral (multi-energy) scan to maintain a given focal spot size (within tolerance) during the entire spectral (multi-energy) scan.

Figure 1:
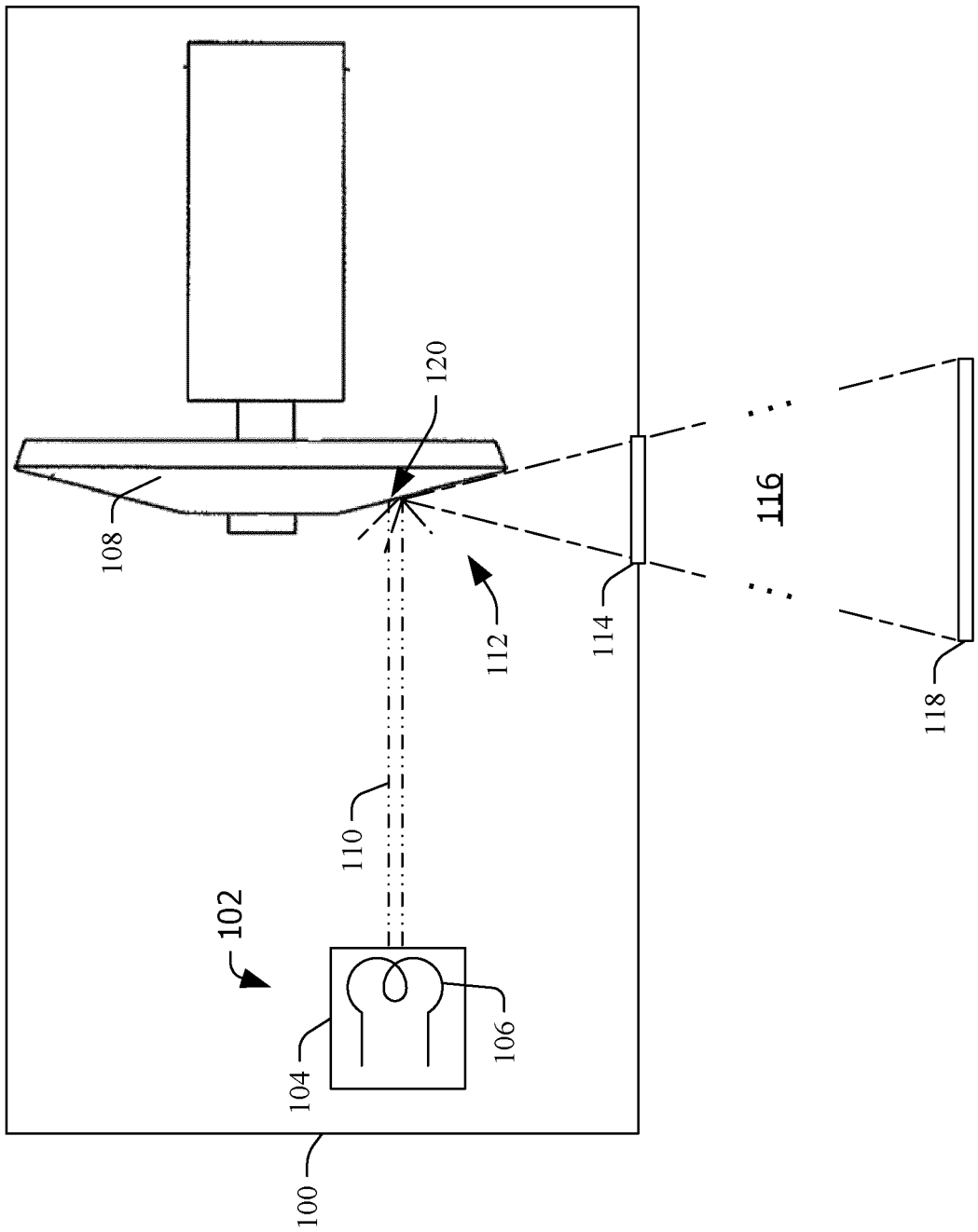
FIG. 1 diagrammatically depicts certain elements of an example X-ray tube.
Figure 2:
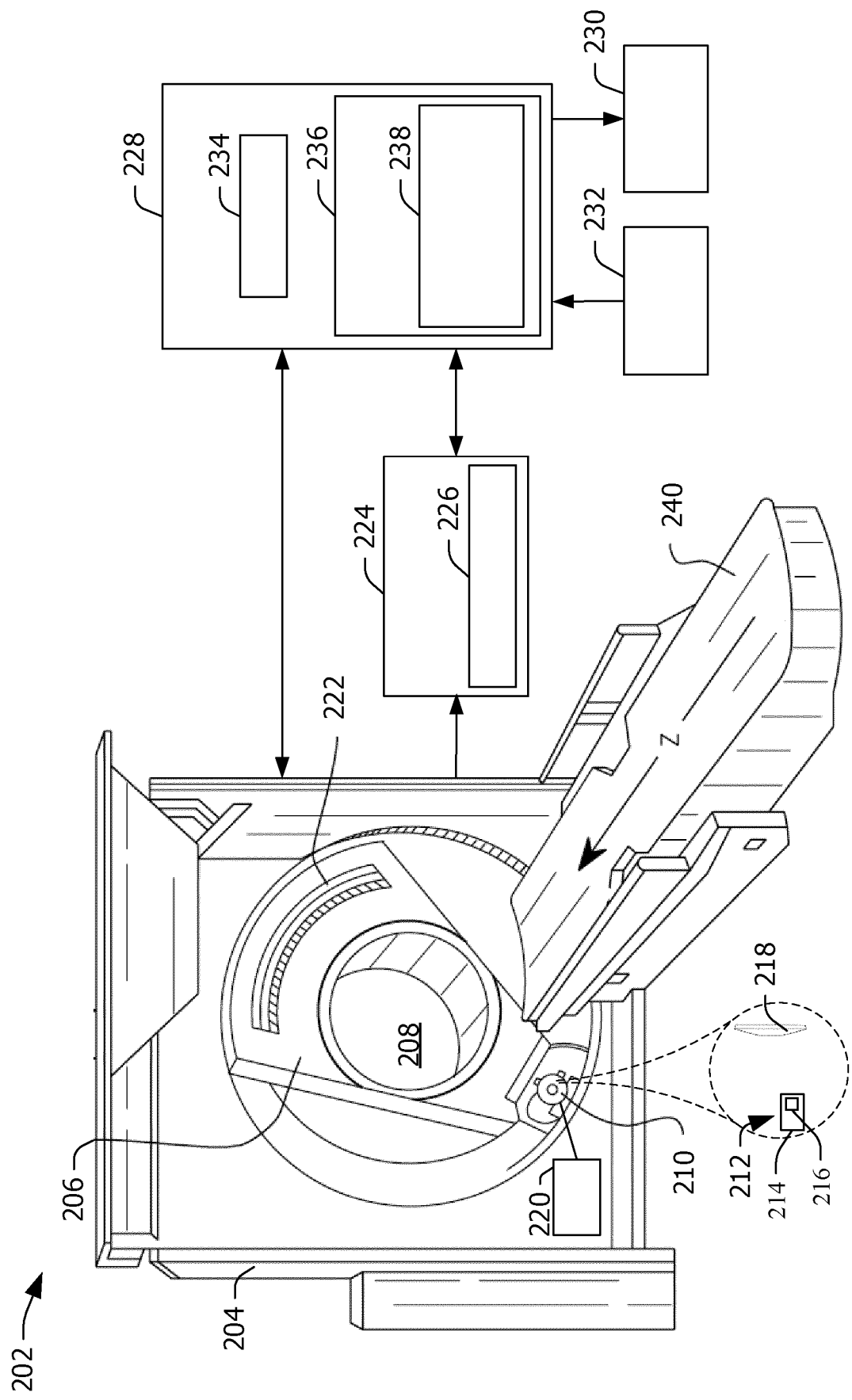
FIG. 2 diagrammatically illustrates an example imaging system configured to maintain a given focal spot size of interest during a kVp switched spectral (multi-energy) scan, in accordance with an embodiment(s) described herein.

FIG. 2 diagrammatically illustrates an imaging system 202, such as a computed tomography (CT) scanner. The imaging system 202 includes a generally stationary gantry 204 and a rotating gantry 206, which is rotatably supported by the stationary gantry 204 and rotates around an examination region 208 about a z-axis "Z".

A radiation source 210, such as an X-ray tube, is rotatably supported by the rotating gantry 206, rotates with the rotating gantry 206 around the examination region 208, and emits X-ray radiation that traverses the examination region 208. The radiation source 210 includes a cathode 212 with a focusing cup 214 and at least one a filament 216 and an anode 218 and is configured for kVp switching during a spectral scan, e.g., between data acquisition periods, within a data acquisition period, etc.

A controller ("CTRL") 220 controls the radiation source 210, including at least a kVp applied across the cathode 212 and the anode 218 and a grid voltage applied across electrodes of the focusing cup 214. In the illustrated embodiment, the controller 220 includes a mapping that maps kVps to grid voltages for each available focal spot size. As described in greater detail below, for kVp switching, the controller 220, for each kVp for a scan, including transitions between kVps, applies the corresponding grid voltage from the mapping so that the grid voltage follow the X-ray tube peak voltage during the spectral scan based on the mapping. In one instance, switching the grid voltage in coordination with switching the kVp ensures that the given focal spot size for the scan is maintained (within tolerance) for the entire kVp switched spectral (multi-energy) scan. As such, the approach described herein mitigates degradation of image quality (artifact into and/or a decreased spatial resolution) and/or anode damage, relative to a configuration in which the grid voltage is not controlled as such.

A detector 222 includes a one- or two-dimensional array of rows of elements, each row extending in an x-y plane, and each row arranged with respect to each other along the z-axis, and each row including one or more detection layers. The detector 222 is rotatably supported by the rotating gantry 206 along an angular arc opposite the radiation source 210 across the examination region 208. The detector 222 rotates in coordination with the radiation source 210, detects radiation that traverses the examination region 208, and generates a different set of projection data (line integrals) for each kVp.

A reconstructor 224 includes a projection domain (PD) decomposer 226 configured to decompose the projection data into different contributions such as photo-electric effect and Compton scattering and/or other bases. The reconstructor 224 reconstructs the decomposed projection data to generate spectral and non-spectral volumetric image data. Examples of spectral volumetric image data include low and high energy, mono-energetic, virtual non-contrast, effective Z (atomic number), iodine only, etc. In one instance, the reconstructor 224 is implemented with a processor (e.g., a central processing unit (CPU), a microprocessor (µCPU), etc.) configured to execute computer executable instructions stored, embedded, encoded, etc. on computer readable storage medium (which excludes transitory medium), such as physical memory and/or other non-transitory memory. The reconstructor 224 is part of the system 202 as shown and/or remote therefrom.

An operator console 228 includes an output device 230 such as a display monitor, a filmer, etc. and an input device 232 such as a keyboard, mouse, etc. The console 228 further includes a processor 234 (e.g., a CPU, µCPU, GPU, etc.) and computer readable storage medium 236 (which excludes transitory medium) such as physical memory. In this example, the computer readable storage medium 236 also includes an image domain (IM) decomposition module 238 for performing the decomposition in the image domain instead of the projection domain (PD). In a variation, the system 202 includes only one of the PD decomposer 226 or the IM decomposition module 238. The operator console 228 allows an operator to control an operation of the system 202 such as selecting a kVp switching imaging protocol, etc.

A subject support 240, such as a couch, supports an object or subject in the examination region 208. The subject support 240 is movable in coordination with performing an imaging procedure so as to guide the subject or object with respect to the examination region 208 for loading, scanning, and/or unloading the subject or object.

As briefly described above, the controller 220 controls at least the kVp and the grid voltage during a kVp switched spectral scan to maintain a given focal spot size for the entire scan. The following describes an example for a dual-energy kVp switched spectral scan.

Figure 3:
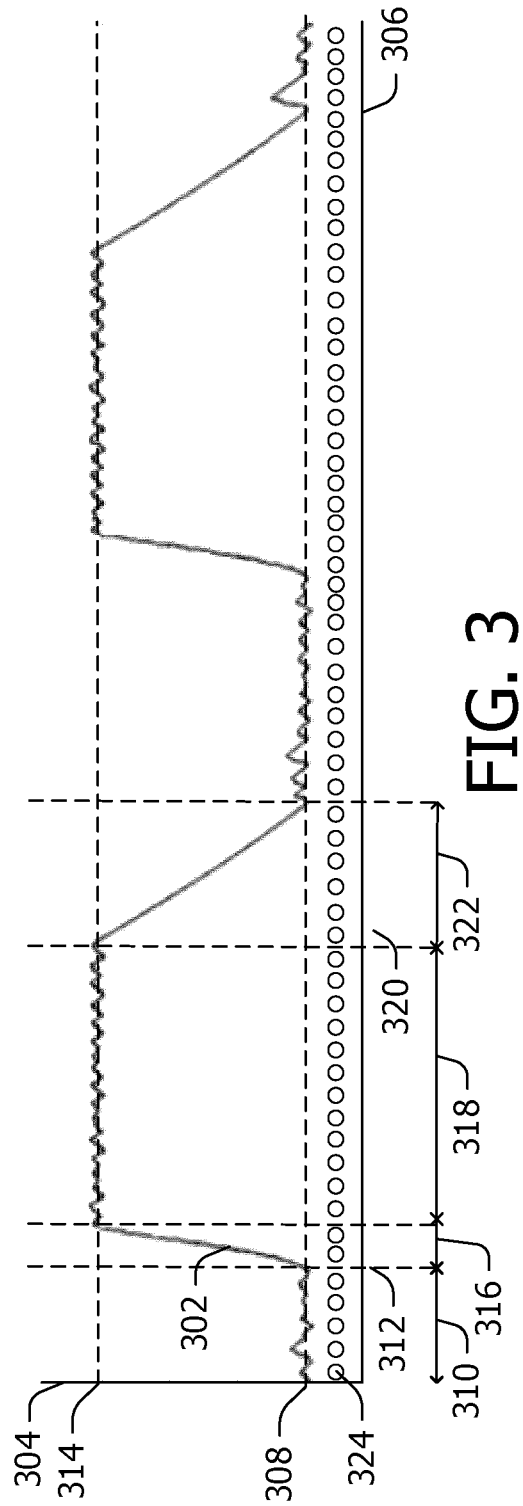
FIG. 3 shows an example plot of kVp as a function of time for a dual energy scan using a grid voltage that changes with kVp along with a graphic representing focal spot size, in accordance with an embodiment(s) described herein.

FIG. 3 shows a plot 302 of kVp as a function of time. A first axis 304 represents kVp. A second axis 306 represents time. In this example, a first kVp 308 is applied during a first time duration 310. At a first time 312, the controller 220 switches the kVp from the first kVp 308 to a second kVp 314. During a second time duration 316, the kVp transitions from the first kVp 308 to the second kVp 314 takes place. During a third time duration 318, the second kVp 314 continues to be applied. At a second time 320, the controller 220 switches the kVp from the second kVp 314 to the first kVp 308. During a fourth time duration 322, the kVp transitions to the first kVp 308 takes place. This pattern repeats for the dual energy scan.

In this example, the controller 220 identifies and applies the grid voltage corresponding to the first kVp 308 during the first time duration 310, each grid voltage corresponding to each kVp transition during the second time duration 316, the grid voltage corresponding to the second kVp 314 during the third time duration 318, and each grid voltage corresponding to each kVp transition during the fourth time duration 322. The controller 220 identifies the grid voltages from the mapping, which can be stored in the controller 220 (and/or the console 228). Also shown in FIG. 3, is a graphic 324, for each time duration, with a size corresponding to the focal spot size. As shown, a size of the graphic 324 is the same (within a tolerance) across the time durations.

In one instance, where the first kVp 308 is 80 kVp and the second kVp is 140 kVp, the transitions between the first kVp 308 and the second kVp 314 (i.e. the second time duration 316) is on an order of fifty microseconds (50 µs) to one hundred microseconds (100 µs). Depending on the actual emission current, the transitions between the second kVp 314 and the first kVp 308 (i.e. the fourth time duration 322) is on an order of one hundred and fifty microseconds (150 µs) to three hundred microseconds (300 µs).

An example integration period (IP) may be on the order of one hundred and fifty microseconds (150 µs) to two hundred and fifty microseconds (250 µs). In general, an IP refers to a period of time when the detector 222 detects radiation while rotating through a predetermined angular increment for a measurement. For each IP, each detector element produces a line integral, a set of line integrals for an IP/angular increment is a view, and the projection data includes a set of views acquired over at least 180° plus a fan angle for each of the different energy spectrums.

Figure 4:
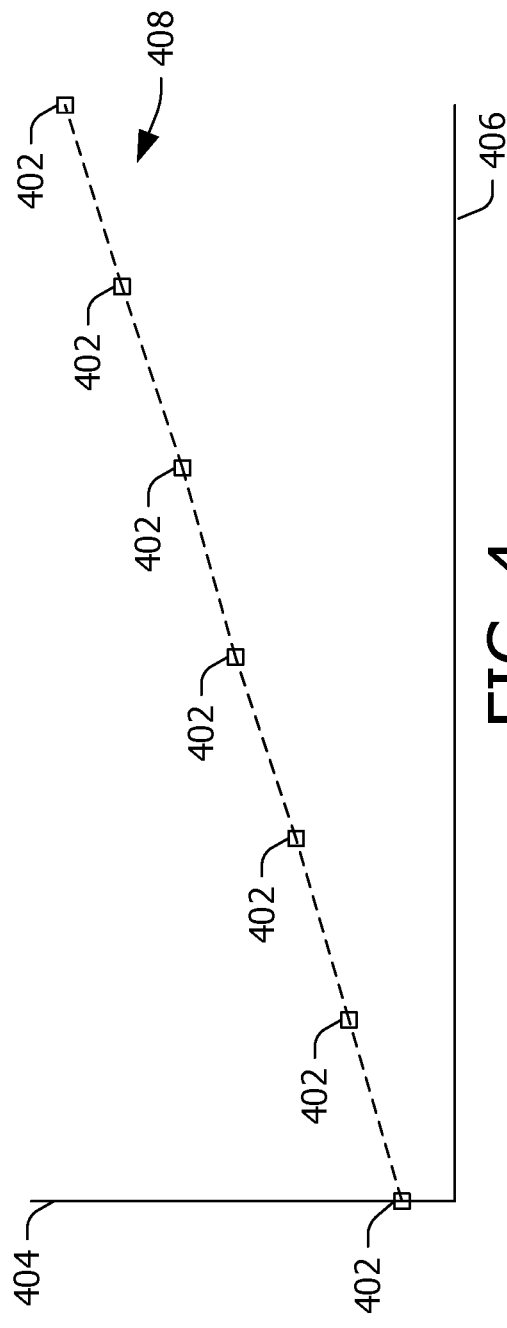
FIG. 4 shows a mapping of grid voltage to kVp for a given focal spot size, in accordance with an embodiment(s) described herein.

In one instance, the mapping between kVps and grid voltages for each focal spot size is determined during manufacture. For this, in one instance, a scan is performed at a given kVp and the focal spot size is measured for different grid voltages. This is repeated for a set of kVps. A mapping between the kVp and the grid voltages for a particular focal spot size can be determined from this data. This can be repeated for other focal spot sizes. FIG. 4 shows an example plot of a set of measured points 402 that maps grid voltages (first axis 404) to kVps (second axis 406) for a given focal spot size.

Interpolation and/or other technique can be used to estimate grids voltage for kVps between the measured points 402 to generate a curve 408. The curve 408 can be stored as the LUT, polynomial, and/or otherwise in the controller 220 and/or elsewhere, e.g., in the memory 236 of the console 228. Continuing with the above example, where the first kVp 308 is 80 kVp and the second kVp is 140 kVp, the grid voltages, in one instance, may range from a few hundred volts (400-800 V) to a few thousand voltages (1000 V-2000 V).

The adjustment of the grid voltage can be achieved with standard and/or specialized electronics without introducing a noticeable delay between kVp values and grid values. In one instance, the bandwidth of the grid voltage control is below ten megahertz (10 MHz). The focal spot size will be constant because the correct grid voltage is applied for each kVp value. A rapid change of grid voltage does not occur at any time point. Risk of uncertainties in the spectrum due to unknown emission currents arising due to random delays in the switching of the grid voltages is suppressed. In the illustrated embodiment, the kVp is switched electrostatically. In a variation, the kVp is switched electromagnetically.

For comparative purposes, FIG. 5 shows a simulated plot 502 of kVp 504 as a function of time 506 for a dual energy scan using only a single constant grid voltages (only for the lower kVp) along with a graphic 508 representing focal spot size. FIG. 5 shows the focal spot size increases (relative to the desired focal spot size) in a region 510 outside of regions 512 corresponding to the lower kVp. FIG. 6 shows a simulated plot 602 of kVp 604 as a function of time 606 for a dual energy scan using only a single constant grid voltages (only for the higher kVp) along with a graphic 608 representing focal spot size. FIG. 6 shows the focal spot size decreases (relative to the desired focal spot size) in regions 610 outside of region 612 corresponding to the higher kVp. As discussed herein, these situations may lead to image artifact, reduce spatial resolution and/or anode damage.

Figure 7:
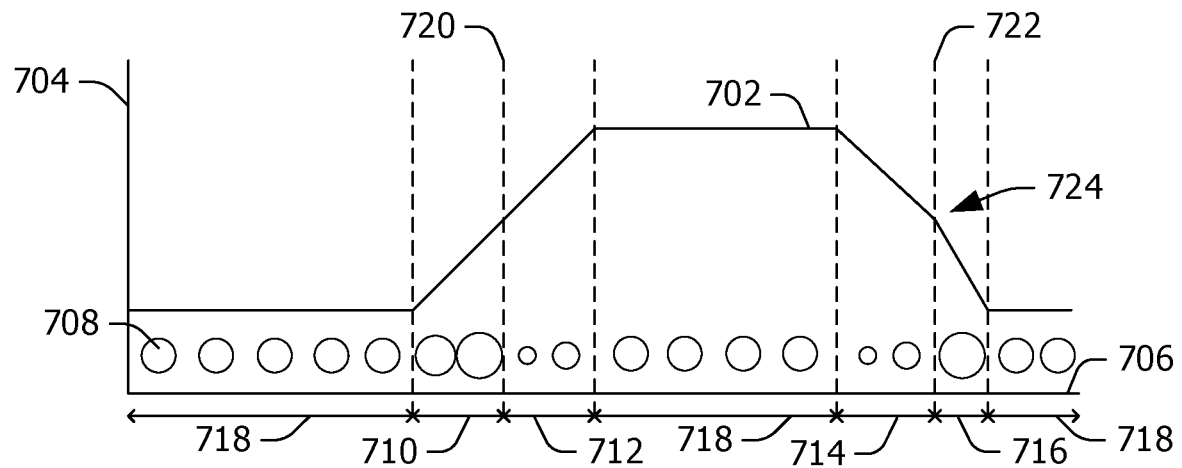
FIG. 7 shows a simulated plot of kVp as a function of time for dual energy scans using two discrete grid voltages (one for a lower kVp and one for a higher kVp) along with a graphic representing focal spot size.

FIG. 7 shows another simulated plot 702 of kVp 704 as a function of time 706 for a dual energy scan using only two discrete grid voltages, one for the lower kVp and one for the higher kVp, along with a graphic 708 representing focal spot size. FIG. 7 shows the focal spot size changes (relative to the desired focal spot size) in regions 710, 712, 714 and 716 outside of regions 718 corresponding to the lower and higher kVps. In this example, the grid voltage is switched at 720 and 722 during the transitions between kVps.

As a consequence, the focal spot size is too large in the region 710 as the kVp increases from the lower kVp voltage towards the higher kVp and the grid voltage for the lower kVp is maintained. In addition, the focal spot size is too small in the region 712 as the kVp continues to increase towards the higher kVp and the grid voltage is now maintained for the higher kVp. In addition, the focal spot size is too small in the region 714 as the kVp now decreases from the higher kVp voltage towards the lower kVp and the grid voltage for the higher kVp is maintained. In addition, the focal spot size is too large in the region 716 as the kVp continues to decrease towards the lower kVp and the grid voltage is now maintained for the lower kVp.

The emission current decreases with an increasing grid voltages and increases with an increasing kVp. The transition from higher to lower kVp is mainly driven by the discharge of the electrodes by the emission current. Changes of the emission current during the transition will changes the slope of the kVp as this transition as shown by the change in slope at 724. Here, the switching of the grid voltage from high to low increases the emission current by this the velocity of the discharge of the electrodes.

Figure 8:
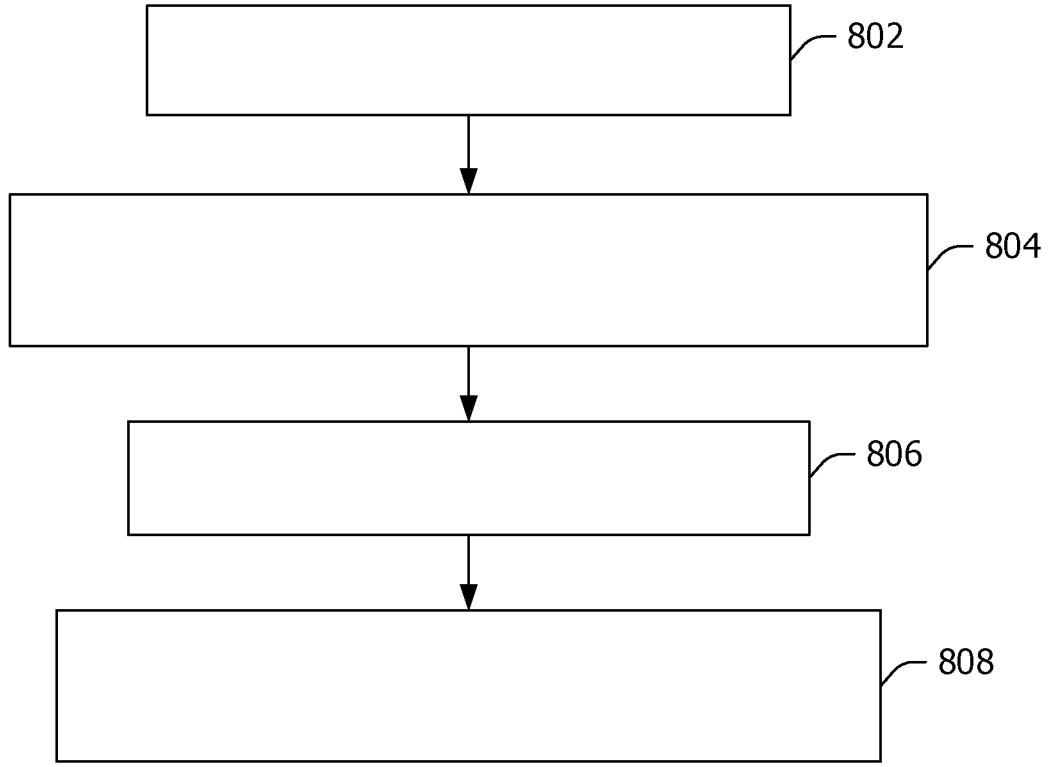
FIG. 8 illustrates an example method for kVp switching.

FIG. 8 illustrates an example method in accordance with an embodiment(s) described herein and/or otherwise.

At 802, the controller 220 applies a first kVp across the cathode 212 and the anode 218 and a corresponding first grid voltage across electrodes of the focusing cup as described herein and/or otherwise.

At 804, the controller 220 transitions the kVp to a second kVp and concurrently transitions the first grid voltage to a corresponding second grid voltage based on a mapping between kVps and grid voltages, as described herein.

At 806, the controller 220 applies the second kVp across the cathode 212 and the anode 218 and the corresponding second grid voltage across electrodes of the focusing cup, as described herein and/or otherwise.

At 808, the controller 220 transitions the kVp back to the first kVp and concurrently transitions second grid voltage back to the first grid voltage based on a mapping between kVps and grid voltages, as described herein and/or otherwise.

One or more of the above acts is performed until the scan is complete. Once complete, the kVp and grid voltage are removed.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An imaging system, comprising:
an X-ray radiation source configured to emit radiation that traverses an examination region; and
a controller configured to:
control an X-ray tube peak voltage of the X-ray radiation source to switch between at least two different X-ray tube peak voltages during a kVp switched spectral scan; and
control a grid voltage of the X-ray radiation source to follow the X-ray tube peak voltage during the spectral scan, wherein the controller is configured to adjust the grid voltage based on a predetermined mapping between a currently applied X-ray tube peak voltage and a corresponding grid voltage for a particular focal spot size such that the particular focal spot size is maintained throughout the spectral scan, wherein the mapping is between X-ray tube peak voltages and grid voltages for each respective focal spot size of a plurality of focal spot sizes.

2. The system of claim 1, wherein the X-ray radiation source comprises:
a cathode including:
a focusing cup with grid electrodes; and
at least one filament; and
an anode; and
wherein the controller is configured to alternately apply the at least two different X-ray tube peak voltages across the cathode and the anode and the grid voltages across the grid electrodes.

3. The system of claim 1, wherein the mapping is represented in a look-up table, and the controller includes the look-up table.

4. The system of claim 1, wherein the mapping is represented as a polynomial, and the controller includes the polynomial.

5. The system of claim 1, wherein the at least two different X-ray tube peak voltages include 80 kilovolts and 140 kilovolts.

6. The system of claim 1, wherein at least two different grid voltages include grid voltages in a range of 400-800 volts and 1000-2000 volts.

7. The system of claim 6, wherein a bandwidth of the grid voltage is less than 10 megahertz.

8. The system of claim 1, wherein a transition from a lower X-ray tube peak voltage to a higher X-ray tube peak voltage is in a range of 50 to 100 microseconds.

9. The system of claim 1, wherein a transition from a higher X-ray tube peak voltage to a lower X-ray tube peak voltage is in a range of 150 to 300 microseconds.

10. The system of claim 1, further comprising:
a detector array configured to detect radiation that traverses the examination region and generate at least first and second sets of line integrals for the at least two different X-ray tube peak voltages.

11. The system of claim 10, further comprising:
a projection domain decomposer configured to decompose the at least first and second sets of line integrals into at least two basis components of interest; and
a reconstructor configured to reconstruct the at least two basis components of interest to generate spectral volumetric image data.

12. The system of claim 10, further comprising:
a reconstructor configured to reconstruct the at least first and second sets of line integrals to generate low and high volumetric image data; and
an image domain decomposition module configured to decompose the low and high volumetric image data into volumetric image data of interest.

13. An image processing method, comprising:
controlling an X-ray tube peak voltage of an X-ray radiation source to switch between at least two different X-ray tube peak voltages during a kVp switched spectral scan; and
controlling a grid voltage of the X-ray radiation source to follow the X-ray tube voltage peak during the spectral scan based on a predetermined mapping between X-ray tube peak voltages and grid voltages for a particular focal spot size in order to maintain the particular focal spot size throughout the spectral scan, wherein the mapping is between X-ray tube peak voltages and grid voltages for each respective focal spot size of a plurality of focal spot sizes.

14. The method of claim 13, wherein the X-ray radiation source comprises:
a cathode including:
a focusing cup with grid electrodes; and
at least one filament; and
an anode, and further comprising:
alternately applying the X-ray tube peak voltages across the cathode and the anode and the grid voltages across the grid electrodes.

15. The method of claim 13, wherein the predetermined mapping is stored in a controller controlling the X-ray radiation source.

16. A non-transitory computer-readable storage medium storing computer executable instructions, which when executed by a processor, cause the processor to:
control an X-ray tube peak voltage of an X-ray radiation source to switch between at least two different X-ray tube peak voltages during a kVp switched spectral scan; and
control a grid voltage of the X-ray radiation source to follow the X-ray tube peak voltage during the spectral scan based on a predetermined mapping between X-ray tube peak voltages and grid voltages for a particular focal spot size to maintain the particular focal spot size throughout the spectral scan, wherein the mapping is between X-ray tube peak voltages and grid voltages for each respective focal spot size of a plurality of focal spot sizes.

17. The non-transitory computer-readable storage medium of claim 16, wherein the X-ray radiation source comprises:
a cathode, including:
a focusing cup with grid electrodes; and
at least one filament; and
an anode, and further comprising:
wherein the processor alternately applies the X-ray tube peak voltages and the grid voltages respectively across the cathode and the anode and the grid electrodes.

18. The non-transitory computer-readable storage medium of claim 16, wherein the predetermined mapping is stored in a memory accessed by the processor.

* * * * *